United States Patent
Hagfors et al.

(10) Patent No.: US 11,369,306 B2
(45) Date of Patent: Jun. 28, 2022

(54) SYSTEM AND METHOD FOR DISPLAYING ELECTROPHYSIOLOGICAL SIGNALS FROM MULTI-DIMENSIONAL CATHETERS

(71) Applicant: St. Jude Medical, Cardiology Division, Inc., St. Paul, MN (US)

(72) Inventors: Mark Hagfors, North Oaks, MN (US); Don Curtis Deno, Andover, MN (US); Luke Chen, Roseville, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 407 days.

(21) Appl. No.: 16/560,640

(22) Filed: Sep. 4, 2019

(65) Prior Publication Data

US 2020/0077908 A1    Mar. 12, 2020

Related U.S. Application Data

(60) Provisional application No. 62/729,081, filed on Sep. 10, 2018.

(51) Int. Cl.
*A61B 5/339* (2021.01)
*A61B 5/00* (2006.01)
(Continued)

(52) U.S. Cl.
CPC .............. *A61B 5/339* (2021.01); *A61B 5/276* (2021.01); *A61B 5/287* (2021.01); *A61B 5/327* (2021.01);
(Continued)

(58) Field of Classification Search
CPC ......... A61B 5/339; A61B 5/327; A61B 5/276; A61B 5/287
See application file for complete search history.

(56) References Cited

U.S. PATENT DOCUMENTS

| 4,649,924 A | 3/1987 | Taccardi |
| 5,297,549 A | 3/1994 | Beatty et al. |

(Continued)

FOREIGN PATENT DOCUMENTS

| EP | 1166714 | 1/2002 |
| EP | 1336379 | 8/2003 |

(Continued)

OTHER PUBLICATIONS

International Search Report and Written Opinion for PCT Application No. PCT/US2018/027607, dated Sep. 12, 2018 (12 pages).
(Continued)

*Primary Examiner* — David E Choi
(74) *Attorney, Agent, or Firm* — Wiley Rein LLP (57) ABSTRACT

A method of displaying a virtual electrogram for a virtual bipole includes receiving a plurality of electrophysiological signals from a respective plurality of electrodes carried by a multi-dimensional catheter; using the received electrophysiological signals to compute a plurality of virtual electrograms associated with a respective plurality of virtual bipoles, each having a corresponding virtual bipole orientation; selecting a virtual bipole orientation; and displaying the virtual electrogram associated with the virtual bipole having the selected virtual bipole orientation. Aspects of the disclosure can be executed through a graphical user interface of an electroanatomical mapping system that also incorporates a visualization processor.

24 Claims, 5 Drawing Sheets

(51) Int. Cl.
 *A61B 5/276* (2021.01)
 *A61B 5/287* (2021.01)
 *A61B 5/327* (2021.01)
 *G06F 3/04845* (2022.01)
 *G06F 3/04847* (2022.01)

(52) U.S. Cl.
 CPC ........ *A61B 5/6859* (2013.01); *G06F 3/04845* (2013.01); *G06F 3/04847* (2013.01)

(56) References Cited

U.S. PATENT DOCUMENTS

| | | | |
|---|---|---|---|
| 5,546,270 | A | 8/1996 | Konno et al. |
| 5,697,377 | A | 12/1997 | Wittkampf |
| 5,848,972 | A | 12/1998 | Friedman et al. |
| 5,921,923 | A | 7/1999 | Kuck et al. |
| 5,983,126 | A | 11/1999 | Wittkampf |
| 6,233,476 | B1 | 5/2001 | Strommer et al. |
| 6,360,121 | B1 | 3/2002 | Shoda et al. |
| 6,400,981 | B1 | 6/2002 | Govari |
| 6,498,944 | B1 | 12/2002 | Ben-Haim et al. |
| 6,640,119 | B1 | 10/2003 | Budd et al. |
| 6,690,963 | B2 | 2/2004 | Ben-Haim et al. |
| 6,728,562 | B1 | 4/2004 | Budd et al. |
| 6,788,967 | B2 | 9/2004 | Ben-Haim et al. |
| 6,939,309 | B1 | 9/2005 | Beatty et al. |
| 6,947,785 | B1 | 9/2005 | Beatty et al. |
| 6,978,168 | B2 | 12/2005 | Beatty et al. |
| 6,990,370 | B1 | 1/2006 | Beatty et al. |
| 7,197,354 | B2 | 3/2007 | Sobe |
| 7,263,397 | B2 | 8/2007 | Hauck et al. |
| 7,386,339 | B2 | 6/2008 | Strommer et al. |
| 7,885,707 | B2 | 2/2011 | Hauck |
| 8,725,241 | B2 | 5/2014 | Ramanathan et al. |
| 8,862,213 | B2 | 10/2014 | Lo et al. |
| 8,876,817 | B2 | 11/2014 | Avitall et al. |
| 10,888,236 | B2 * | 1/2021 | Ruppersberg ........ A61B 5/6857 |
| 11,089,987 | B2 * | 8/2021 | Spector ................. A61B 5/361 |
| 11,096,617 | B2 * | 8/2021 | Han ...................... A61B 5/7203 |
| 11,160,481 | B2 * | 11/2021 | Zeidan ............... A61B 18/1492 |
| 11,172,858 | B2 * | 11/2021 | Olson ..................... A61B 34/20 |
| 2006/0253030 | A1 | 11/2006 | Altmann et al. |
| 2007/0225589 | A1 | 9/2007 | Viswanathan |
| 2008/0183088 | A1 | 7/2008 | Lian et al. |
| 2008/0221643 | A1 | 9/2008 | Olson |
| 2009/0248014 | A1 | 10/2009 | Shachar et al. |
| 2010/0168557 | A1 | 7/2010 | Deno et al. |
| 2010/0168560 | A1 | 7/2010 | Hauck et al. |
| 2013/0190747 | A1 | 7/2013 | Avitall et al. |
| 2013/0274582 | A1 | 10/2013 | Afonso et al. |
| 2014/0058375 | A1 | 2/2014 | Koblish |
| 2014/0235996 | A1 | 8/2014 | Kim et al. |
| 2014/0336518 | A1 | 11/2014 | Shuros et al. |
| 2014/0343442 | A1 | 11/2014 | Thakur et al. |
| 2016/0015294 | A1 * | 1/2016 | Friedman ............... A61B 5/352 600/374 |
| 2016/0045133 | A1 | 2/2016 | Balachandran et al. |
| 2016/0033147 | A1 | 11/2016 | Deno et al. |
| 2017/0042449 | A1 | 2/2017 | Deno et al. |
| 2017/0049348 | A1 | 2/2017 | Deno et al. |
| 2019/0209034 | A1 * | 7/2019 | Deno ...................... A61B 5/339 |
| 2019/0239765 | A1 * | 8/2019 | Fuentes-Ortega ... A61B 5/6859 |
| 2019/0239766 | A1 * | 8/2019 | Fuentes-Ortega ... A61B 5/6859 |
| 2019/0239810 | A1 * | 8/2019 | Solis ..................... A61B 5/6859 |
| 2020/0077908 | A1 * | 3/2020 | Hagfors ................. A61B 5/287 |

FOREIGN PATENT DOCUMENTS

| | | |
|---|---|---|
| EP | 2186474 | 5/2010 |
| JP | 11047148 | 2/1999 |
| JP | 2001-061789 | 3/2001 |
| JP | 2002-051998 | 2/2002 |
| JP | 2002-067713 A | 3/2002 |
| JP | 2007537831 | 12/2007 |
| JP | 2012524606 | 10/2012 |
| WO | 1997/024983 | 7/1997 |
| WO | 2007146864 | 12/2007 |
| WO | 2010058372 | 5/2010 |
| WO | 2012/037471 | 3/2012 |
| WO | 2012-092016 | 7/2012 |
| WO | 2014/113612 | 7/2014 |
| WO | 2014/182822 | 11/2014 |
| WO | 2015/130824 | 9/2015 |
| WO | 2015/150022 A1 | 10/2015 |
| WO | 2016/183247 | 11/2016 |

OTHER PUBLICATIONS

Mazeh et al., "A Simplified Approach for Simultaneous Measurements of Wavefront Velocity and Curvature in the Heart Using Activation Times," Cardiovascular Engineering and Technology, 4:4 (Dec. 2013) pp. 520-534.

Michaud et al., "Information at our Catheter Tips: Unipolar Electrogram Morphology Makes another Comeback!", Heart Rhythm, 7:9 (Sep. 2010) pp. 1301-1302.

Mironov et al., "Role of Conduction Velocity Restitution and Short-Term Memory in the Development of Action Potential Duration Alternans in Isolated Rabbit Hearts", Circulatoin (Jul. 1, 2008), pp. 17-25.

Mountantonakis et al., "Relationship between Voltage Map "Channels" and the Location of Critical Isthmus Sites in Patients with Post-Infarction Cardiomyopathy and Ventricular Tachycardia", JACC 61:20 (May 21, 2013), pp. 2088-2095.

Nanthakumar et al., "Regional Differences in Ventricular Fibrillation in the Open-Chest Porcine Left Ventricle", Circulation Research (Oct. 18, 2002), pp. 733-740.

Narayan et al., "Treatment of Atrial Fibrillation by the Ablation of Localized Sources", JACC 60:7 (Aug. 14, 2012), pp. 628-636.

Nayyar et al., "High-Density Mapping of Ventricular Scar A Comparison of Ventricular Tachycardia (VT) Supporting Channels with Channels that do not Support VT", Circulation (Feb. 2014), pp. 90-98.

Otomo et al., "Local Unipolar and Bipolar Electrogram Criteria for Evaluating the Transmurality of Atrial Ablation Lesions at Different Catheter Orientations Relative to the Endocardial Surface", Heart Rhythm 7:9 (Sep. 2010), pp. 1291-1300.

Parson et al., "Cardiac Mapping Instrumentation for the Instantaneous Display of Endocardial and Epicardial Activiation", IEEE Transactions on Biomedical Engineering, vol. BME-34, No. 6 (Jun. 1987), pp. 468-472.

Patel et al., "Electroanatomic Mapping of the Intercaval Bundle in Atrial Fibrillation", Circulation (Dec. 2014), pp. 1262-1267.

Pieper et al., "Simultaneously Collected Monopolar and Discrete Bipolar Electrograms: Comparison of Activation Time Detection Algorithms", PACE, vol. 16 (Mar. 1993), pp. 426-433.

Plank et al., "Cardiac Near-Field Morphology During Conduction Around a Microscopic Obstacle-a Computer Simulation Study", Annals of Biomedical Engineering, 31:10 (Nov. 2003), pp. 1206-1212.

Plank et al., "Model Study of Vector-Loop Morphology During Electrical Mapping of Microscopic Conduction in Cardiac Tissue", Annals of Biomedical Engineering, 28:10 (Oct. 2000), pp. 1244-1252.

Plank et al., "Use of Cardiac Electric Near-Field Measurements to Determine Activation Times", Annals of Biomedical Engineering, 31:9 (Oct. 2003) pp. 1066-1076.

Price et al., "Novel Ablation Catheter Technology that Improves Mapping Resolution and Monitoring of Lesion Maturation", The Journal of Innovations in Cardiac Rhythm Management, (Jan. 2012), pp. 599-609.

Ravelli et al., "Wave Similarity Mapping Shows the Spatiotemporal Distribution of Fibrillatory Wave Complexity in the Human Right Atrium During Paroxysmal and Chronic Atrial Fibrillation", Journal of Cardiovascular Electrophysiology, 16:10 (Oct. 2005), pp. 1071-1076.

Rogers et al., "Quantitative Techniques for Analyzing High-Resolution Cardiac-Mapping Data", IEEE Engineering in Medicine and Biology, 17:1 (Jan./Feb. 1998), pp. 62-72.

(56) References Cited

OTHER PUBLICATIONS

Schilling et al., "Simultaneous Endocardial Mapping in the Human Left Ventricle Using a Noncontact Catheter Comparison of Contact and Reconstructed Electrograms During Sinus Rhythm", Circulation (Sep. 1, 1998), pp. 887-898.
Schmitt et al., "Symposium on Electrocardiography and Vectorcardiography the Present Status of Vectorcardiography", JAMA Internal Medicine 96:5 (Nov. 1955), pp. 574-590.
Schuler et al., "Influence of Catheter Orientation, Tissue Thickness and Conduction Velocity on the Intracardiac Electrogram", Biomed Tech 2013; 58 (Suppl. 1), 2 pages.
Schumacher et al., "Transverse Conduction Capabilities of the Crista Terminalis in Patients with Atrial Flutter and Atrial Fibrillation", JACC 34:2 (Aug. 1999), pp. 363-373.
Shors et al., "A Method for Determining High-Resolution Activation Time Delays in Unipolar Cardiac Mapping"; IEEE Transactions on Biomedical Engineering, 43:12 (Dec. 1996), pp. 1192-1196.
Spears et al., "Relationship of Bipolar and Unipolar Electrogram Voltage to Scar Transmurality and Composition Derived by Magnetic Resonance Imaging in Patients with Nonischemic Cardiomyopathy Undergoing VT Ablation", Heart Rhythm 9:11 (Nov. 2012), pp. 1837-1846.
Stevenson et al., "Recording Techniques for Clinical Electrophysiology", Journal of Cardiovascular Electrophysiology 16:9 (Sep. 2005), pp. 1017-1022.
Tedrow et al., "Recording and Interpreting Unipolar Electrograms to Guide Catheter Ablation", Heart Rhythm 8:5 (May 2011), pp. 791-796.
Thompson et al., "Improved Spatial Resolution and Electrgram Wave Direction Independence with the Use of an Orthogonal Electrode Configuration", J Clin Monit Comput 28: (Apr. 2014), pp. 157-163.
Tungjikusolmun et al., "Guidelines for Predicting Lesion Size at Common Endocardial Locations During Radio-Frequency Ablation", IEEE Transactions on Biomedical Engineering 48:2 (Feb. 2001), pp. 194-201.
Weber et al., "Conduction Velocity Restitution of the Human Atrium—An Efficient Measurement Protocol for Clinical Electrophysiological Studies"; IEEE Transactions on Biomedical Engineering, 58:9 (Sep. 2011), pp. 2648-2655.
Witkowski et al., "In Vivo Estimation of Cardiac Transmembrane Current", Circulation Research 72:2 (Feb. 1993), pp. 424-439.
Yamada et al., "Electrophysiological Pulmonary Vein Antrum Isolation with a Multielectrode Basket Catheter is Feasible and Effective for Curing Paroxysmal Atrial Fibrillation: Efficacy of Minimally Extensive Pulmonary Vein Isolation", Heart Rhythm, 3:4 (Apr. 2006), pp. 377-384.
Yamada, "Pulmonary Vein Isolation with a Multielectrode Basket Catheter"; Indian Pacing and Electropysiology Journal, 7(2) (2006), pp. 97-109.
Zaman et al., "The Rotor Revolution Conduction at the Eye of the Storm in Atrial Fibrillation", Circulation (Dec. 2014), pp. 1230-1236.
Zhang et al., "Noninvasive Three-Dimensional Electrocardiographic Imaging of Ventricular Activation Sequence", Am J Physiol Heart Circ Physiol, vol. 289 (Aug. 5, 2005), pp. H2724-H2732.
International Search Report and Written Opinion for PCT Application No. PCT/US2018/027607, dated Sep. 12, 2018 (16 pages).
Anter et al., "High-Resolution Mapping of Scar-Related Atrial Arrhythmias Using Smaller Electrodes with Closer Interelectrode Spacing", Circulation 8:3 (Jun. 2015), 31 pages.
Arora et al., "Fundamentals of Intracardiac Mapping", Catheter Ablation of Cardia Arrhythimias (2006), pp. 107-134.
Avitall et al., "Maximal Electrogram Attenuation recorded from Mini Electrodes Embedded on 4.5-mm Irrigated and 8-mm Nonirrigated Catheters Signifies Lesion Maturation", Journal of Cardiovascular Electrophysiology 26:2 (Feb. 2015), pp. 1-11.
Balasundaram et al., "Tracking Rotors with Minimal Electrodes: Modulation Index Based Stragegy", Circulation 8:2 (Apr. 2, 2015), 34 pages.

Barnette et al., "Estimation of a 3-D Conduction Velocity Vector Fields from Cardiac Mapping Data", Computers in Cardiology, vol. 25 (Sep. 1998), pp. 605-608.
Bayly et al.., "Estimation of Conduction Velocity Vector Fields from Epicardial Mapping Data", IEEE Transactions on Biomedical Engineering, 45:5 (May 1998), pp. 563-571.
Bayly et al., "Estimation of Conduction Velocity Vector Fields from 504-Channel Epicardial Mapping Data", Computers in Cardiology (Sep. 1996), pp. 133-136.
Benharash, "Quantitative Analysis of Localized Sources Identified by Focal Impulse and Rotor Modulation Mapping in Atrial Fibrillation", Circulation (Jun. 2015), pp. 554-561.
Bharati et al., "The Conduction System of the Swine Heart", Chest 100:1 (Jul. 1991), pp. 207-212.
Bortone et al., "Unipolar Signal Modification as a Guide for Lesion Creation During Radiofrequency Application in the Left Atrium Prospective Study in Humans in the Setting of Paroxysmal Atrial Fibrillation Cather Ablation", Circulation (Dec. 2013), pp. 1095-1102.
Bouman et al., "Structure and Function of the Sino-Atrial Node: A Review", European Heart Journal 7:2 (Feb. 1986), pp. 94-104.
Boyett et al., "The Sinoatrial Node, a Heterogeneous Pacemaker Structure", Cardiovascular Research 47:4 (2000), pp. 658-687.
Burch et al., "Chapter X The Development of Spatial Vectrocardiography", A History of Electrocardiography, Norman Publishing (Apr. 1990), pp. 235-248.
Cantwell et al., "Techniques for Automated Local Activation Time Annotation and Conduction Velocity Estimation in Cardiac Mapping", Computers in Biology and Medicine (Oct. 1, 2015), pp. 1-14.
Casella et al., "Feasibility of Combined Unipolar and Bipolar Voltage Maps to Improve Sensitivity of Endomycardial Biopsy", Circulation (Jun. 2015) 36 pages.
Chan et al., "The Effect of Ablation Length and Catheter Tip to Endocardial Orientation on Radiofrequency Lesion Size in the Canine Right Atrium", PACE 25:1 (Jan. 2002), pp. 4-13.
Damle et al., "Atrial and Accessory Pathway Activation Direction in Patients with Orthodromic Supraventricular Tachycardia: Insights from Vector Mapping", JACC 23:3 (Mar. 1, 1994), pp. 684 692.
De Bakker et al., "The Pathophysiologic Basis of Fractionated and Complex Electrograms and the Impact of Recording Techniques on Their Detection and Interpretation", Circulation (Apr. 2010) 3: pp. 204-213.
Deng et al., "Simulation of Biatrial Conduction via Different Pathways during Sinus Rhythm with a Detailed Human Atrial Model", Journal of Zhjiang University—Science B (Biomedicine & Biotechnology) Sep. 2012, 13(9): pp. 376-694.
Deng et al., "An Image-Based Model of the Whole Human Heart with Detailed Anatomical Structure and Fiber Orientation", Computational and Mathematical Methods in Medicine, vol. 2012; Jul. 2012, 16 pages.
Desai et al., "Two Phase Radiofrequency Catheter Ablation of Isolated Ventricular Endomyocardium", PACE vol. 14, (Jul. 1991), pp. 1179-1194.
Dubois et al., "Global and Directional Activation Maps for Cardiac Mapping in Electrophysiology", Computing in Cardiology (Sep. 2012), 39: pp. 349-352.
Faes et al., "A Method for Quantifying Atrial Fibrillation Organization Based on Wave-Morphology Similarity", IEEE Transactions on Biomedical Engineering, 49:12, (Dec. 2002), pp. 1504-1513.
Fedotov et al., "Methods for Increasing the Reliability of Coordinate Determination by the Location and Imaging Systems of Endocardial Electrodes", Biomedical Engineering 41:4 (Jul. 2007), pp. 145-149.
Fisher et al., "Three-Dimensional Electrogram Mapping Improves Ablation of Left-Sided Accessory Pathways", PACE vol. 15 (Dec. 1992), pp. 2344-2356.
Fitzgerald et al., "Comparative Psychometric Analysis of Vector and Isochrone Cardiac Activation Maps", IEEE Transactions on Biomedical Engineering 51:5 (May 2004) pp. 847-855.
Fitzgerald et al., "Estimation of Cardiac Conduction Velocities Using Small Data Sets", Annals of Biomedical Engineering, vol. 31 (Mar. 2003), pp. 250-261.

(56) References Cited

OTHER PUBLICATIONS

Fitzgerald et al., "Identification of Cardiac Rhythm Features by Mathematical Analysis of Vector Fields", IEEE Transactions on Biomediccal Engineering 52:1 (Jan. 2005), pp. 19-29.

Gaudette et al., "Epicardial Velocity Estimation Using Wavelets", Computers in Cardiology 24 (Sep. 1997), pp. 339-342.

Gerstenfeld et al., "Detection of Changes in Atrial Endocardial Activation with Use of an Orthogonal Catheter", JACC 18:4 (Oct. 1991) pp. 1034-1042.

Gerstenfeld et al., "Evidence for Transient Linking of Atrial Excitation During Atrial Fibrillation in Humans", Circulation 86:2 (Aug. 1992), pp. 375-382.

Gornick et al., "Validation of a New Noncontact Catheter System for Electroanatomic Mapping of Left Ventricular Endocardium", Circulation (1999) 99: 829-835.

Gupta et al., "Rapid Ablation of Recurrent Atrial Flutter Using a Novel Ablation Catheter", The Journal of Innovations in Cardiac Rhythm Management (Nov. 2014), No. 5, pp. 1808-1812.

Haddad et al., "Novel Algorithmic Methods in Mapping of Atrial and Ventricular Tachycardia", Circulation (Jun. 2011), 29 pages.

Harrild et al., "A Computer Model of Normal Conduction in the Human Atria", Circulation Research (Sep. 29, 2000), 12 pages.

Horner et al., "Electrode for Recording Direction of Activation, Conduction Velocity, and Monophasic Action Potential of Myocardium", the American Physiological Society (Apr. 1997), pp. H1917-H1927.

Huang et al., "Evolution of the Organization of Epicardial Activation Patterns During Ventricular Fibrillation", Journal of Cardiovascular Electrophysiology (Dec. 1998) 9:12, pp. 1291-1304.

Ideker et al., "The Assumptions of Isochronal Cardiac Mapping", PACE, vol. 12 (Mar. 1989), pp. 456-478.

Irie et al., "Relationship Between Sinus Rhythm Late Activation Zones and Critical Sites for Scar-Related Ventricular Tachycardia: A Systematic Analysis of Isochronal Late Activation Mapping", Circulation (Apr. 2015), 32 pages.

Kadish et al., "Mapping of Atrial Activation with a Noncontact, Multielectrode Catheter in Dogs", Circulation (1999) 99: pp. 1906-1913.

Kadish et al., "Vector Mapping of Myocardial Activation", Circulation (Sep. 1986) 74:3, pp. 603-615.

Karney et al., "Quaternions in Molecular Modeling", Journal of Molecular Graphics and Modeling 25 (Jan. 2007), pp. 595-604.

Kay et al., "Measuring Curvature and Velocity Vector Fields for Waves of Cardiac Excitation in 2-D Media", IEEE Transactions on Biomedical Engineering 52:1 (Jan. 2005) pp. 50-63.

Kearsley, "On the Orthogonal Transformation Used for Structural Comparisons", Acta Cryst (Feb. 1, 1989) Section A45, pp. 208-210.

Kumar et al., "Unipolar Electrogram Morphology to Assess Lesion Formation During Catheter Ablation of Atrial Fibrillation Successful Translation into Clinical Practice", Circulation (Dec. 2013) pp. 1050-1052.

Lindsay et al., "Novel Directional Activation Map Using Local Propagation Between Adjacent Electrograms", Heart Rhythm 8:5 (May Supplement 2011), 2 pages.

Liu et al., "Three-Dimensional Imaging of Ventricular Activation and Electrograms from Intracavitary Recordings", IEEE Transactions on Biomedial Engineering 58:4 (Apr. 2011), pp. 868-875.

Liu et al., "Functional Characterization of the Crista Terminalis in Patients with Atrial Flutter: Implications of Radiofrequency Ablation", JACC 43:9 (May 5, 2004), pp. 1639-1645.

Mase et al., "Velocity Field Analysis of Activation Maps in Atrial Fibrillation a Simulation Study", World Congress (Sep. 2009, IFMBE Proceedings 25/IV), pp. 1014-1017.

Weber et al., "Wave-Direction and Conduction-Velocity Analysis from Intracardiac Electrograms—A Single-Shot Technique", IEEE Transactions on Biomedical Engineering, 57:10 (Oct. 2010), pp. 2394-2401.

De Bakker et al., "Activation Mapping: Unipolar Versus Bipolar Recording", Cardiac Electrophysiology—From Cell to Bedside—Second Edition ISBN 0-7216-4941-6, pp. 1068-1078.

International Preliminary Report on Patentability received for PCT Patent Application No. PCT/US2019/49547, dated Mar. 25, 2021 (13 pages).

Deno, et al., "Orientation-Independent Catheter-Based Characterization of Myocardial Activation", IEEE Transactions on Biomedical Engineering, vol. 64, No. 5 (May 1, 2017), pp. 1067-1077.

Haldar, et al., "Resolving Bipolar Electrogram Voltages During Atrial Fibrillation Using Omnipolar Mapping", Circulation, vol. 10, No. 9 (Sep. 1, 2017), 17 pages.

Jude, St., et al.,"EnSite Precision(TM) Cardiac Mapping System Model EE3000", Retrieved from: URL:https://manuals.sjm.com/~/media/manuals/product-manual-pdfs/, 1200 pages, Jan. 12, 2016.

Fogel, "C-P004-01 to C-P004-220", Heart Rhythm, vol. 14, No. 5 (May 10, 2017), 91 pages.

\* cited by examiner

SYSTEM AND METHOD FOR DISPLAYING ELECTROPHYSIOLOGICAL SIGNALS FROM MULTI-DIMENSIONAL CATHETERS

CROSS-REFERENCE TO RELATED APPLICATIONS

This application claims the benefit of U.S. provisional application No. 62/729,081, filed 10 Sep. 2018, which is hereby incorporated by reference as though fully set forth herein.

BACKGROUND

The present disclosure relates generally to electrophysiological mapping, such as may be performed in cardiac diagnostic and therapeutic procedures. In particular, the present disclosure relates to systems, apparatuses, and methods for displaying electrophysiological signals measured by multi-dimensional catheters, such as high density ("HD") grid catheters.

It is known to visualize electrode traces (e.g., intracardiac electrogram traces) measured using an electroanatomical mapping system. For example, the traces can be stacked vertically on a display, with the order of the traces corresponding to the order of electrodes on the electrophysiology catheter.

This approach to displaying electrode traces is logical for electrophysiology catheters that include electrodes arranged along a single axis, because linear catheters provide a natural sorting direction along the catheter spline (e.g., most proximal to most distal or vice versa). With the increased usage of electrophysiology catheters that include electrodes arranged along multiple axes and/or in two- or three-dimensions, such as HD grid catheters, Carto® PentaRay® catheters (Biosense Webster, Inc., Irvine, Calif.) and/or spiral catheters, however, the approach described above may not be as logical.

Moreover, it is known that the morphology and amplitude of a bipolar electrogram is sensitive to bipole orientation (in the case of a linear catheter, bipole orientation corresponds to catheter orientation). Yet, it can be difficult or complicated to orient the catheter in a desired direction. Multi-dimensional catheters can alleviate these complications, but there remains a need to define the desired bipole orientation even when measured using a multi-dimensional catheter.

BRIEF SUMMARY

Disclosed herein is a method of displaying a virtual electrogram for a selected virtual bipole. The method includes: receiving, at an electroanatomical mapping system, a plurality of electrophysiological signals from a respective plurality of electrodes carried by a multi-dimensional catheter; using the plurality of received electrophysiological signals, computing, via the electroanatomical mapping system, a plurality of virtual electrograms associated with a respective plurality of virtual bipoles, wherein each virtual bipole of the plurality of virtual bipoles has a corresponding virtual bipole orientation; selecting a virtual bipole orientation via the electroanatomical mapping system; and displaying the virtual electrogram associated with the virtual bipole having the selected virtual bipole orientation via the electroanatomical mapping system.

According to aspects of the disclosure, the step of selecting a virtual bipole orientation includes the electroanatomical mapping system generating a graphical user interface and receiving a user selection of the virtual bipole orientation through the graphical user interface. For instance, the graphical user interface can include an orientation selection dial, an orientation slider, a geometric model of a patient's anatomy, and/or a graphical representation of the multi-dimensional catheter. In embodiments where the graphical user interface includes a geometric model of the patient's anatomy, the step of receiving a user selection of the virtual bipole orientation through the graphical user interface can include receiving a user's definition of the virtual bipole orientation on the geometric model of the patient's anatomy. Similarly, in embodiments where the graphical user interface includes a graphical representation of the multi-dimensional catheter, the step of receiving a user selection of the virtual bipole orientation through the graphical user interface can include receiving a user's definition of the virtual bipole orientation on the graphical representation of the multi-dimensional catheter.

Alternatively or additionally, the step of selecting a virtual bipole orientation can include the electroanatomical mapping system identifying a virtual bipole associated with a maximum amplitude virtual electrogram.

It is contemplated that the virtual electrogram associated with the virtual bipole having the selected virtual bipole orientation can be added to an electrophysiology map. Likewise, it is contemplated that the method can include outputting a graphical representation of the electrophysiology map on a three-dimensional geometric model. The graphical representation can also include a graphical representation of the selected virtual bipole orientation (e.g., on the three-dimensional geometric model and/or on a graphical representation of the multi-dimensional catheter thereon or therein).

Also disclosed herein is a method of displaying a virtual electrogram for a selected virtual bipole. The method includes: defining, via an electroanatomical mapping system, a clique of three or more electrodes carried by a multi-dimensional catheter; using a plurality of electrophysiological signals received from the clique of three or more electrodes carried by the multi-dimensional catheter, computing, via the electroanatomical mapping system, a plurality of virtual electrograms, wherein each virtual electrogram of the plurality of virtual electrograms is associated with a respective virtual bipole having a bipole orientation relative to the multi-dimensional catheter; selecting a virtual bipole orientation via the electroanatomical mapping system; and displaying, via the electroanatomical mapping system, the virtual electrogram associated with the virtual bipole having the selected virtual bipole orientation as its bipole orientation relative to the multi-dimensional catheter.

In embodiments of the disclosure, the step of selecting a virtual bipole orientation includes the electroanatomical mapping system generating a graphical user interface and receiving a user selection of the virtual bipole orientation through the graphical user interface. The graphical user interface can include an orientation selection dial; an orientation selection slider, a geometric model of a patient's anatomy, and/or a graphical representation of the multi-dimensional catheter. In embodiments where the graphical user interface includes a geometric model of the patient's anatomy, the step of receiving a user selection of the virtual bipole orientation through the graphical user interface can include receiving a user's definition of the virtual bipole orientation on the geometric model of the patient's anatomy. Likewise, in embodiments where the graphical user interface includes a graphical representation of the multi-dimensional catheter, the step of receiving a user selection of the virtual bipole orientation through the graphical user interface can include receiving a user's definition of the virtual bipole orientation on the graphical representation of the multi-dimensional catheter.

Alternatively, the step of selecting a virtual bipole orientation can include the electroanatomical mapping system identifying a virtual bipole associated with a maximum amplitude virtual electrogram.

According to aspects of the disclosure, the virtual electrogram associated with the virtual bipole having the selected virtual bipole orientation as its bipole orientation relative to the multi-dimensional catheter can be added to an electrophysiology map, with a location of the virtual electrogram within the electrophysiology map determined by a position of the clique of three or more electrodes. For instance, the location of the virtual electrogram within the electrophysiology map can be determined by a centroid of the clique of three or more electrodes.

It is contemplated that the clique of three or more electrodes can include all electrodes carried by the multi-dimensional catheter.

The instant disclosure also provides a system for displaying a plurality of virtual electrograms for a respective plurality of virtual bipoles. The system includes an electroanatomical mapping system configured to receive a plurality of electrophysiological signals from a respective plurality of electrodes carried by a multi-dimensional catheter. The electroanatomical mapping system further includes a visualization module configured to: compute a plurality of virtual electrograms associated with a respective plurality of virtual bipoles using the plurality of received electrophysiological signals, wherein each virtual bipole of the plurality of virtual bipoles has a corresponding virtual bipole orientation; select a virtual bipole orientation; and display the virtual electrogram associated with the virtual bipole having the selected virtual bipole orientation.

The visualization module can be configured to select the virtual bipole orientation by: generating a graphical user interface for selection of the virtual bipole orientation; and receiving a user selection of the virtual bipole orientation through the graphical user interface. Alternatively or additionally, the visualization module can be configured to select the virtual bipole orientation by identifying a virtual bipole associated with a maximum amplitude virtual electrogram.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 4A through 4C depict various graphical user interfaces ("GUI") through which a practitioner or user can select a virtual bipole orientation for display. More particularly.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for displaying electrophysiological signals measured using a multi-dimensional catheter. For purposes of illustration, aspects of the disclosure will be described with reference to displaying electrophysiological signals measured using an HD grid catheter, such as the Advisor™ HD Grid Mapping Catheter, Sensor Enabled™ from Abbott Laboratories (Abbott Park, Ill.), in the context of a cardiac mapping procedure carried out using an electrophysiology mapping system (e.g., using an electroanatomical mapping system such as the EnSite Precision™ cardiac mapping system, also from Abbott Laboratories). It should be understood, however, that the teachings herein can be applied to good advantage in other contexts and/or with respect to other electrode configurations.

Figure 1:
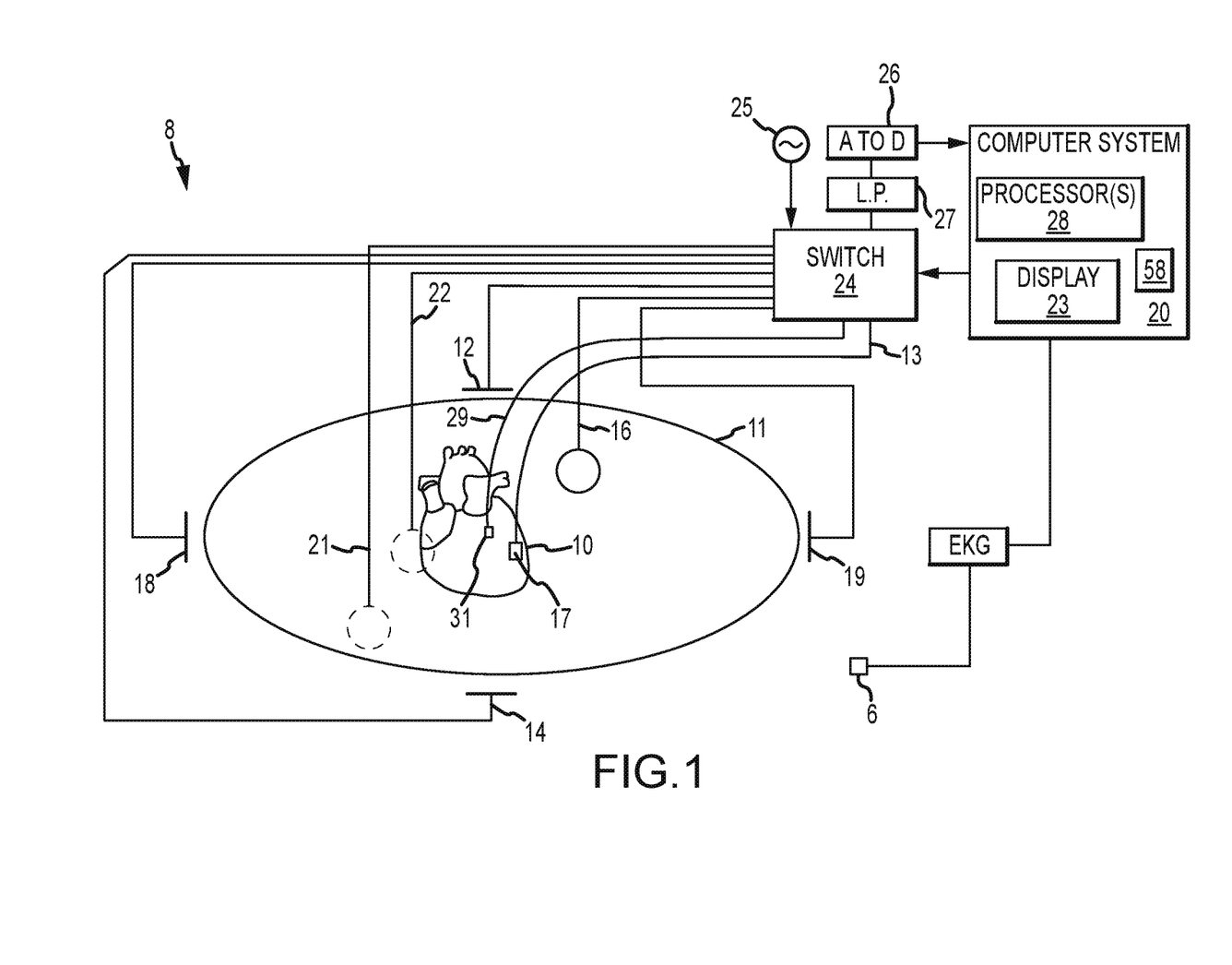
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes.

Figure 2:
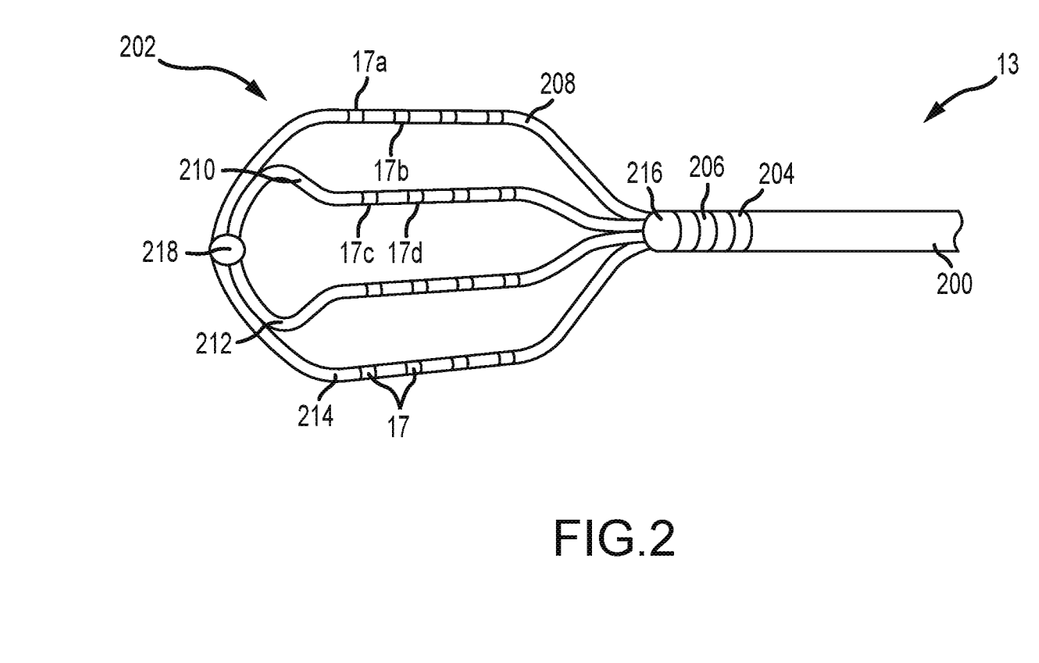
FIG. 2 depicts an exemplary catheter that can be used in connection with aspects of the instant disclosure.

The foregoing embodiments are merely exemplary, however, and any number of electrodes and/or catheters may be used. For example, for purposes of this disclosure, a segment of an exemplary multi-electrode catheter, and in particular an HD grid catheter, is shown in FIG. 2. HD grid catheter 13 includes a catheter body 200 coupled to a paddle 202. Catheter body 200 can further include first and second body electrodes 204, 206, respectively. Paddle 202 can include a first spline 208, a second spline 210, a third spline 212, and a fourth spline 214, which are coupled to catheter body 200 by a proximal coupler 216 and to each other by a distal coupler 218. In one embodiment, first spline 208 and fourth spline 214 can be one continuous segment and second spline 210 and third spline 212 can be another continuous segment. In other embodiments, the various splines 208, 210, 212, 214 can be separate segments coupled to each other (e.g., by proximal and distal couplers 216, 218, respectively). It should be understood that HD catheter 13 can include any number of splines; the four-spline arrangement shown in FIG. 2 is merely exemplary.

As described above, splines 208, 210, 212, 214 can include any number of electrodes 17; in FIG. 2, sixteen electrodes 17 are shown arranged in a four-by-four array. It should also be understood that electrodes 17 can be evenly and/or unevenly spaced, as measured both along and between splines 208, 210, 212, 214.

Catheter 13 (or multiple such catheters) are typically introduced into the heart and/or vasculature of the patient via one or more introducers and using familiar procedures. Indeed, various approaches to introduce catheter 13 into a patient's heart, such as transseptal approaches, will be familiar to those of ordinary skill in the art, and therefore need not be further described herein.

Since each electrode 17 lies within the patient, location data may be collected simultaneously for each electrode 17 by system 8. Similarly, each electrode 17 can be used to gather electrophysiological data from the cardiac surface (e.g., surface electrograms). The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation of a cardiac geometry and/or of cardiac electrical activity from the plurality of electrophysiology data points. Moreover, insofar as the ordinarily skilled artisan will appreciate how to create electrophysiology maps from electrophysiology data points, the aspects thereof will only be described herein to the extent necessary to understand the present disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation (Marlborough, Mass.), the CARTO navigation and location system of Biosense Webster, Inc. (Irvine, Calif.), the AURORA® system of Northern Digital Inc. (Waterloo, Ontario), Sterotaxis, Inc.'s NIOBE® Magnetic Navigation System (St. Louis, Mo.), as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to displaying graphical representations of electrophysiological signals (e.g., traces of bipolar electrograms) measured by catheter 13, for example on display 23. System 8 can therefore include a visualization module 58 that can be used to generate traces of electrophysiological signals on display 23. Those of ordinary skill in the art will be familiar with the graphical representation of electrophysiological signal traces in conjunction with electroanatomical mapping systems, such that a detailed description of the same is not necessary to an understanding of the instant disclosure.

Figure 3:
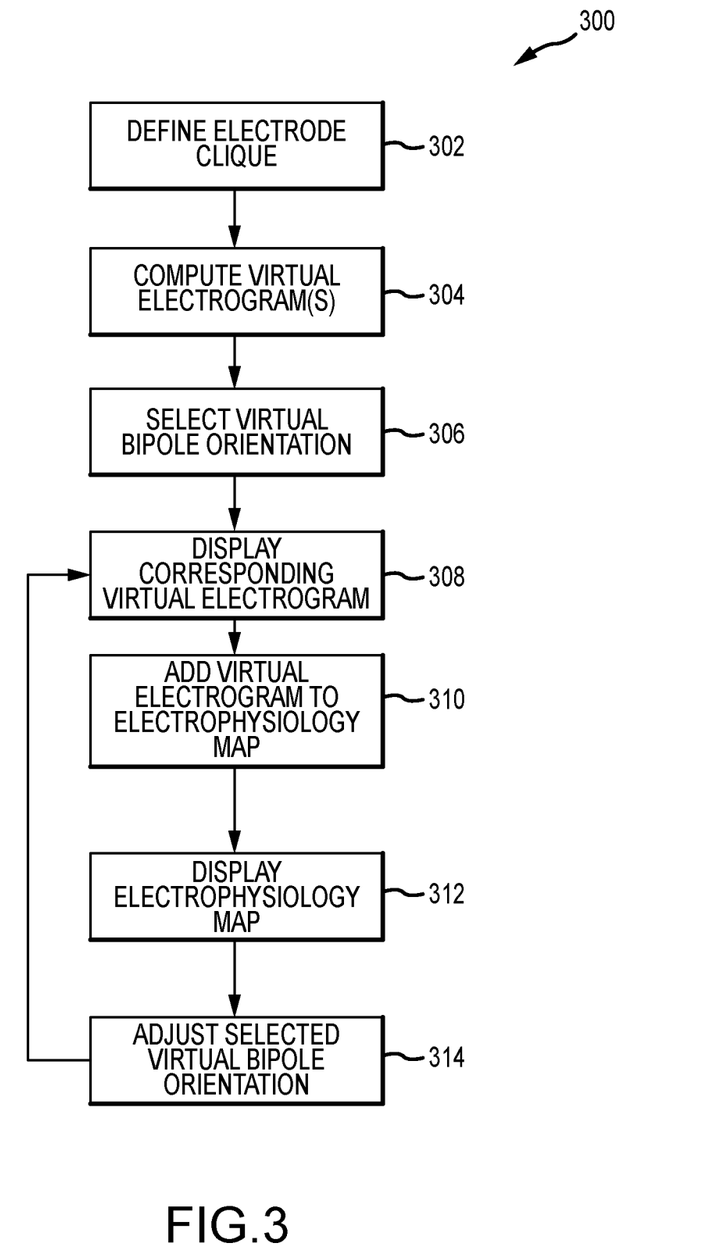
FIG. 3 is a flowchart of representative steps that can be carried out according to exemplary embodiments disclosed herein.

One exemplary method according to the present teachings will be explained with reference to the flowchart 300 of representative steps presented as FIG. 3. In some embodiments, for example, flowchart 300 may represent several exemplary steps that can be carried out by electroanatomical mapping system 8 of FIG. 1 (e.g., by processor 28 and/or visualization module 58). It should be understood that the representative steps described below can be either hardware- or software-implemented. For the sake of explanation, the term "signal processor" is used herein to describe both hardware- and software-based implementations of the teachings herein.

A clique of three or more electrodes 17 carried by catheter 13 is defined in block 302. Consider, for example, a clique of four electrodes 17a, 17b, 17c, 17d as shown in FIG. 2. This clique includes a total of six possible bipoles: 17a-17b and 17c-17d along splines; 17a-17c and 17b-17d across splines; and 17a-17d and 17b-17c diagonally. Similarly, consider a clique of three electrodes 17a, 17b, and 17c as shown in FIG. 2. This clique includes a total of three possible bipoles: 17a-17b along spline 208; 17a-17c across splines; and 17b-17c diagonally.

For purposes of illustrating the instant disclosure, all sixteen electrodes carried by catheter 13 will be regarded as the clique in the following description of the computation of virtual bipoles and their corresponding virtual electrograms. It should be understood, however, that this is merely an exemplary embodiment of the disclosure and not the only embodiment thereof. Indeed, from the following description of a clique of sixteen electrodes, those of ordinary skill in the art will appreciate how to apply the teachings herein to any clique of three or more electrodes.

For the illustrative clique of sixteen electrodes, there are a total of 42 bipoles (12 along splines, 12 across splines, and 18 diagonal between splines). Each bipole can, in turn, be used to generate a bipolar electrogram according to techniques that will be familiar to those of ordinary skill in the art. Moreover, these bipolar electrograms can be combined (e.g., least squares fit linearly combined) to generate electrograms in any direction of the plane of catheter 13 by computing an E-field loop for the clique of electrodes. U.S. application Ser. No. 15/953,155, which is hereby incorporated by reference as though fully set forth herein, discloses details of computing an E-field loop for a clique of electrodes on a HD grid catheter.

In the foregoing regard, system 8 uses the electrophysiological signals received from the clique of electrodes to compute a plurality of electrograms for a corresponding plurality of bipoles having respective orientations relative to catheter 13 in block 304. Each orientation defines a "virtual bipole," and each virtual bipole has a corresponding "virtual electrogram."

In aspects of the disclosure, system 8 can compute a virtual electrogram for each degree in a half-circle (e.g., the virtual bipoles have a resolution of 1 degree). It should be understood, however, that system 8 can compute virtual electrograms with higher resolution (e.g., the spacing between virtual bipoles is less than 1 degree) or lower resolution (e.g., the spacing between virtual bipoles is greater than 1 degree) without departing from the scope of the instant teachings.

A virtual bipole orientation is selected in block 306. Various approaches to selecting the virtual bipole orientation are contemplated. In some embodiments of the disclosure, system 8 generates a graphical user interface through which a practitioner can specify the virtual bipole orientation. For instance, system 8 can display an orientation selection control, such as a dial 402 (FIG. 4A) or slider 404 (FIG. 4B) that allows the practitioner to select the virtual bipole orientation. Dial 402 can include an index marking 406 to assist the practitioner in interpreting the selected virtual bipole orientation.

Figure 4A:
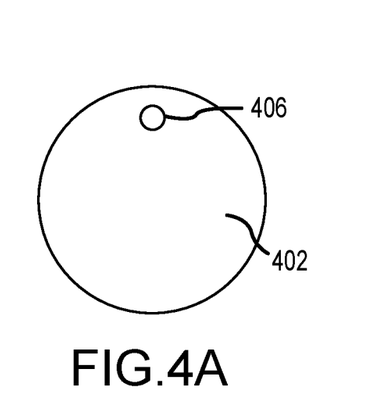
FIG. 4A depicts a virtual bipole orientation selection dial as described in connection with certain aspects of the instant disclosure.
Figure 4B:
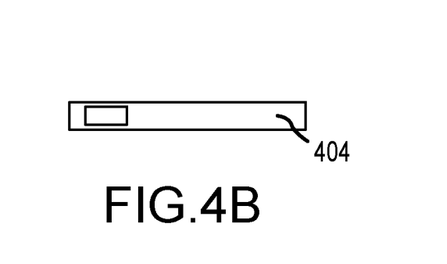
FIG. 4B depicts a virtual bipole orientation selection slider as described in connection with additional aspects of the instant disclosure.
Figure 4C:
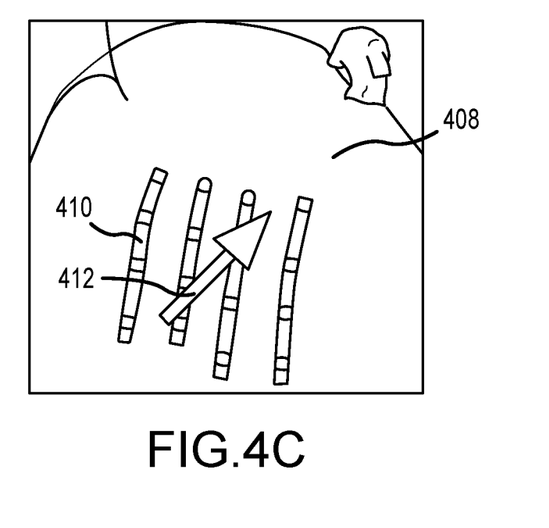
FIG. 4C depicts a graphical representation of an anatomical geometry and/or multi-dimensional catheter as described in still further aspects of the instant disclosure.

As another example, shown in FIG. 4C, system 8 can display a three-dimensional geometric model 408 of a patient's anatomy and/or a graphical representation 410 of catheter 13. The practitioner can have drawn (e.g., using a mouse or other pointing device) and/or adjust the direction of an arrow 412 on model 408 and/or graphical representation 410, where the direction of arrow 412 represents the virtual bipole orientation.

In still other embodiments of the disclosure, system 8 can identify the maximum amplitude virtual electrogram computed in block 304 and automatically select the corresponding bipole orientation.

In yet further embodiments of the disclosure, system 8 can select the bipole orientation that optimizes a desired virtual electrogram property (e.g., minimum fractionation, minimum noise, maximum or minimum cycle length, or the like), other than maximum amplitude as discussed above.

Figure 5:
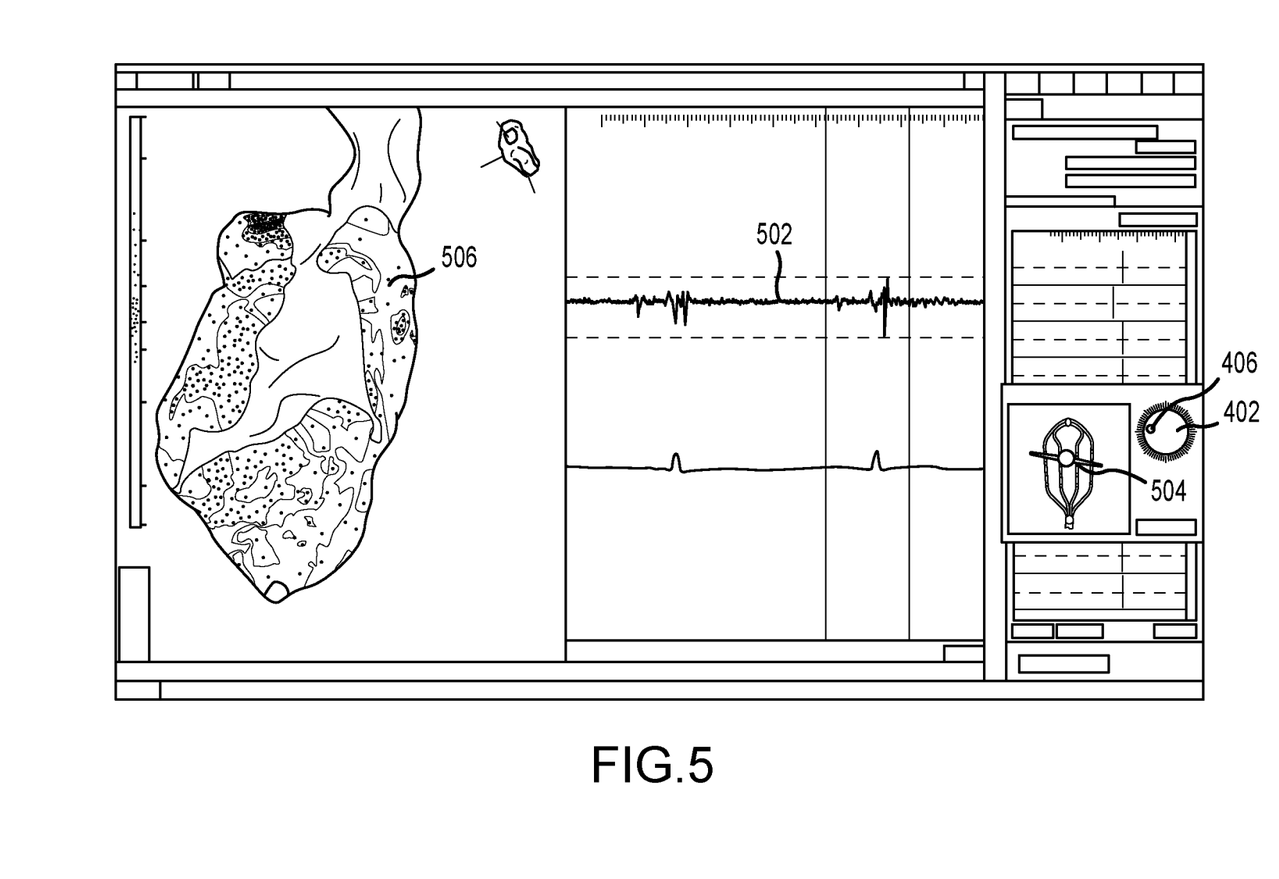
FIG. 5 is a representative GUI and accompanying display of a virtual electrogram and electrophysiology map.

In block 308, a graphical representation of the virtual electrogram corresponding to the selected virtual bipole is displayed. For instance, as shown in FIG. 5, a trace 502 of the virtual electrogram can be output on display 23. FIG. 5 also depicts orientation selection dial 402 and a representation 504 of the orientation of the virtual bipole relative to catheter 13.

System 8 can also add the virtual electrogram to an electrophysiology map in block 310. As will be familiar to those of ordinary skill in the art, an electrophysiology map includes a plurality of electrophysiology data points, each including both location data and electrophysiological data. In aspects of the disclosure, the location to which the virtual electrogram is mapped can be determined by a position of the clique of electrodes. For instance, the virtual electrogram can be mapped to the centroid of the clique of electrodes. In FIG. 5, this mapping is reflected in the position of representation 504 of the orientation of the selected virtual bipole relative to catheter 13.

In block 312, system 8 can output a graphical representation of the electrophysiology map, for example on a three-dimensional cardiac model according to techniques that will be familiar to those of ordinary skill in the art. FIG. 5 depicts a representative electrophysiology map 506.

In block 314, a practitioner can adjust the selected virtual bipole orientation, such as via orientation selection dial 402, slider 404, or the like. Display 23 can then be updated to depict a trace 502 of the virtual electrogram corresponding to the newly-selected virtual bipole orientation. The electrophysiology map, and graphical representation 506 thereof, can also be updated accordingly. In this way, the practitioner can visually inspect and understand how electrophysiological activity varies with the orientation of catheter 13, but advantageously without having to physically re-orient catheter 13.

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to electrophysiology data points collected during an electrophysiology study performed at an earlier time).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of displaying a virtual electrogram for a selected virtual bipole, the method comprising:
   receiving, at an electroanatomical mapping system, a plurality of electrophysiological signals from a respective plurality of electrodes carried by a multi-dimensional catheter;
   using the plurality of received electrophysiological signals, computing, via the electroanatomical mapping system, a plurality of virtual electrograms associated with a respective plurality of virtual bipoles, wherein each virtual bipole of the plurality of virtual bipoles has a corresponding virtual bipole orientation;
   selecting a virtual bipole orientation via the electroanatomical mapping system; and
   displaying the virtual electrogram associated with the virtual bipole having the selected virtual bipole orientation via the electroanatomical mapping system.

2. The method according to claim 1, wherein selecting a virtual bipole orientation comprises the electroanatomical mapping system generating a graphical user interface and receiving a user selection of the virtual bipole orientation through the graphical user interface.

3. The method according to claim 2, wherein the graphical user interface comprises an orientation selection dial.

4. The method according to claim 2, wherein the graphical user interface comprises an orientation selection slider.

5. The method according to claim 2, wherein the graphical user interface comprises a geometric model of a patient's anatomy, and wherein receiving a user selection of the virtual bipole orientation through the graphical user interface comprises receiving a user's definition of the virtual bipole orientation on the geometric model of the patient's anatomy.

6. The method according to claim 2, wherein the graphical user interface comprises a graphical representation of the multi-dimensional catheter, and wherein receiving a user selection of the virtual bipole orientation through the graphical user interface comprises receiving a user's definition of the virtual bipole orientation on the graphical representation of the multi-dimensional catheter.

7. The method according to claim 2, wherein selecting a virtual bipole orientation comprises the electroanatomical mapping system identifying a virtual bipole associated with a maximum amplitude virtual electrogram.

8. The method according to claim 1, further comprising adding the virtual electrogram associated with the virtual bipole having the selected virtual bipole orientation to an electrophysiology map.

9. The method according to claim 8, further comprising outputting a graphical representation of the electrophysiology map on a three-dimensional geometric model.

10. The method according to claim 1, further comprising outputting a graphical representation of the selected virtual bipole orientation.

11. The method according to claim 10, wherein outputting a graphical representation of the selected virtual bipole orientation comprises outputting the graphical representation of the selected virtual bipole orientation on a graphical representation of the multi-dimensional catheter.

12. A method of displaying a virtual electrogram for a selected virtual bipole, the method comprising:
    defining, via an electroanatomical mapping system, a clique of three or more electrodes carried by a multi-dimensional catheter;
    using a plurality of electrophysiological signals received from the clique of three or more electrodes carried by the multi-dimensional catheter, computing, via the electroanatomical mapping system, a plurality of virtual electrograms, wherein each virtual electrogram of the plurality of virtual electrograms is associated with a respective virtual bipole having a bipole orientation relative to the multi-dimensional catheter;
    selecting a virtual bipole orientation via the electroanatomical mapping system; and
    displaying, via the electroanatomical mapping system, the virtual electrogram associated with the virtual bipole having the selected virtual bipole orientation as its bipole orientation relative to the multi-dimensional catheter.

13. The method according to claim 12, wherein selecting a virtual bipole orientation comprises the electroanatomical mapping system generating a graphical user interface and receiving a user selection of the virtual bipole orientation through the graphical user interface.

14. The method according to claim 13, wherein the graphical user interface comprises an orientation selection dial.

15. The method according to claim 13, wherein the graphical user interface comprises an orientation selection slider.

16. The method according to claim 13, wherein the graphical user interface comprises a geometric model of a patient's anatomy, and wherein receiving a user selection of the virtual bipole orientation through the graphical user interface comprises receiving a user's definition of the virtual bipole orientation on the geometric model of the patient's anatomy.

17. The method according to claim 13, wherein the graphical user interface comprises a graphical representation of the multi-dimensional catheter, and wherein receiving a user selection of the virtual bipole orientation through the graphical user interface comprises receiving a user's definition of the virtual bipole orientation on the graphical representation of the multi-dimensional catheter.

18. The method according to claim 12, wherein selecting a virtual bipole orientation comprises the electroanatomical mapping system identifying a virtual bipole associated with a maximum amplitude virtual electrogram.

19. The method according to claim 12, further comprising adding the virtual electrogram associated with the virtual bipole having the selected virtual bipole orientation as its bipole orientation relative to the multi-dimensional catheter to an electrophysiology map, wherein a location of the virtual electrogram within the electrophysiology map is determined by a position of the clique of three or more electrodes.

20. The method according to claim 19, wherein the location of the virtual electrogram within the electrophysiology map is determined by a centroid of the clique of three or more electrodes.

21. The method according to claim 12, wherein the clique of three or more electrodes comprises all electrodes carried by the multi-dimensional catheter.

22. A system for displaying a plurality of virtual electrograms for a respective plurality of virtual bipoles, the system comprising:
    an electroanatomical mapping system configured to receive a plurality of electrophysiological signals from a respective plurality of electrodes carried by a multi-dimensional catheter, wherein the electroanatomical mapping system further comprises a visualization module configured to:
        compute a plurality of virtual electrograms associated with a respective plurality of virtual bipoles using the plurality of received electrophysiological signals, wherein each virtual bipole of the plurality of virtual bipoles has a corresponding virtual bipole orientation;
        select a virtual bipole orientation; and
        display the virtual electrogram associated with the virtual bipole having the selected virtual bipole orientation.

23. The system according to claim 22, wherein the visualization module is configured to select the virtual bipole orientation by:
    generating a graphical user interface for selection of the virtual bipole orientation; and
    receiving a user selection of the virtual bipole orientation through the graphical user interface.

24. The system according to claim 22, wherein the visualization module is configured to select the virtual bipole orientation by identifying a virtual bipole associated with a maximum amplitude virtual electrogram.

* * * * *